United States Patent [19]

Eaton et al.

[11] 4,003,709

[45] Jan. 18, 1977

[54] VISUAL SPOILAGE INDICATOR FOR FOOD CONTAINERS

[75] Inventors: John C. Eaton, Dayton; Marshall B. Kilgore, Franklin; Richard B. Livingston, Dayton, all of Ohio

[73] Assignee: Visual Spoilage Indicator Company, Dayton, Ohio

[22] Filed: Oct. 2, 1975

[21] Appl. No.: 619,017

[52] U.S. Cl. .......................... 23/253 R; 23/254 R; 116/114 AM; 426/87
[51] Int. Cl.² .................................. G01N 31/02
[58] Field of Search ............ 116/114 AM; 73/356; 426/88, 87; 23/254 R, 232 R, 253 R; 99/493

[56] References Cited

UNITED STATES PATENTS

| | | | |
|---|---|---|---|
| 2,951,461 | 9/1960 | Lockwood | 116/114 AM |
| 3,000,706 | 9/1961 | Royce | 23/232 R |
| 3,067,015 | 12/1962 | Lawdermilt | 426/87 X |
| 3,420,635 | 1/1969 | Davis | 99/493 X |
| 3,542,567 | 11/1970 | Finley et al. | 426/87 |
| 3,743,520 | 7/1973 | Croner | 426/87 |

FOREIGN PATENTS OR APPLICATIONS

| | | | |
|---|---|---|---|
| 1,320,583 | 4/1962 | France | 116/114 AM |

Primary Examiner—Richard C. Queisser
Assistant Examiner—Daniel M. Yasich

[57] ABSTRACT

A solution for detecting concentrations of $CO_2$ is sealed within a pouch located on or in a food container and visually observable from outside the container. A microporous material places the indicator in gaseous communication with the food contents of the container, while maintaining isolation from the food liquids and solids. As a result, the indicator is responsive only to $CO_2$ gas evolved within the container, and is unaffected by the particular pH of the food within the container. The $CO_2$ detector provides a visual change when $CO_2$ gas is detected, thus indicating probable deterioration of the food contents of the container.

2 Claims, 12 Drawing Figures

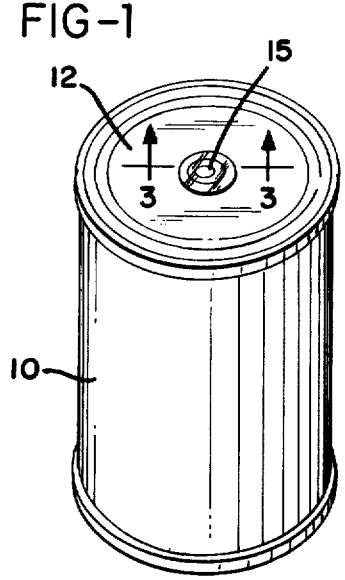
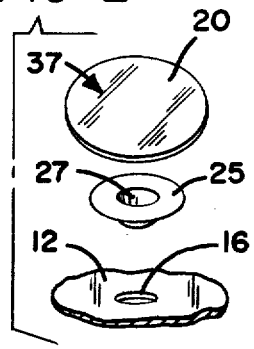
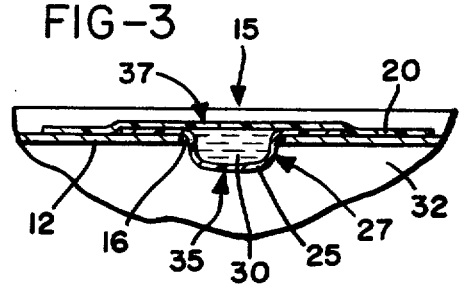
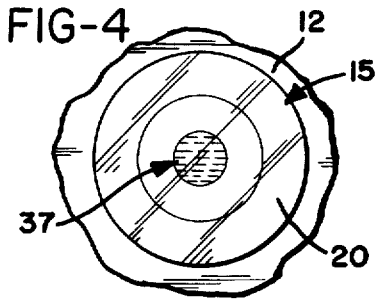
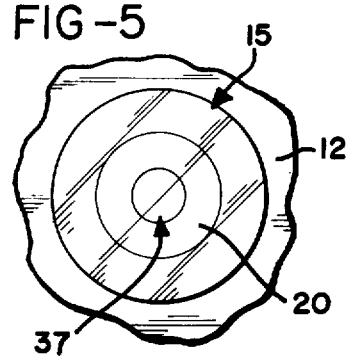
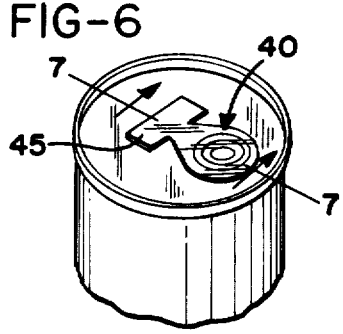
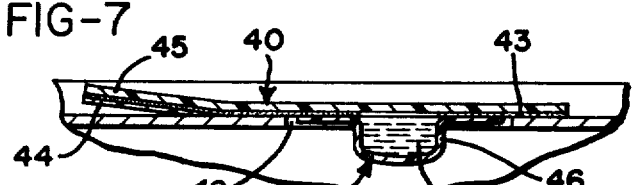
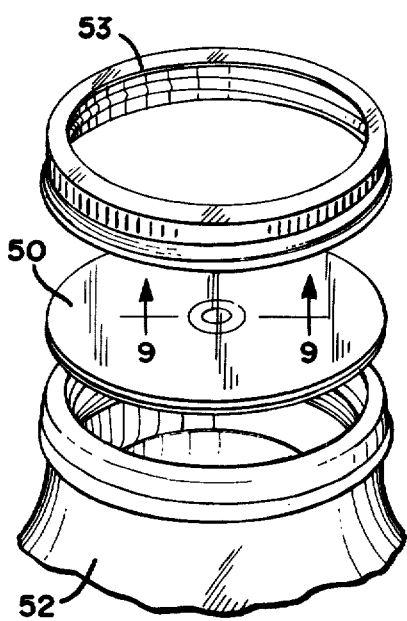
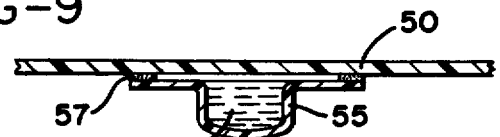
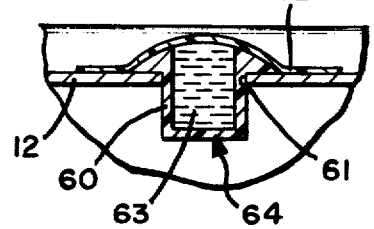
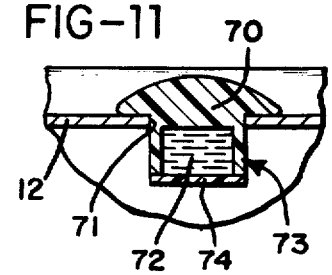

VISUAL SPOILAGE INDICATOR FOR FOOD CONTAINERS

BACKGROUND OF THE INVENTION

This invention relates to visual detection and warning devices, and more particularly to a visual spoilage indicator for food containers. The invention is especially relevant to inexpensive indicators which may be easily incorporated into common food containers to provide a quick and easily detectable indication of probable deterioration of the food contents within the container.

Hardly a year goes by when there is not an outbreak of botulism in some part of the country. Even though the strictest standards of care may be observed in the preparation, packaging, sealing, and sterilization of foodstuffs and their containers, it is virtually impossible to insure completely against the occasional presence of bacteria. Given enough time (and not much is required), even one or just a few bacteria can create a substantial risk of botulism within the contaminated container. Of course, the public is warned to watch for such signs as swollen cans, but more than this is needed, as proven by the many people who continue to be hospitalized from time to time from botulism poisoning.

Recently it has become increasingly common for manufacturers to date code their products so that, either through sale or removal by the grocer, the products will be limited to a reasonable shelf life. This shelf life is presumably determined by balancing the risk that a contaminated container could become dangerous in a given period of time versus the cost of increasing the reliability of production controls in order to reduce the likelihood of initial contamination. Obviously, it would be unreasonably expensive to be absolutely certain that every container which left the factory was completely and totally sterile. On the other hand, a fair quantity of perfectly good food is probably destroyed when the shelf life expires in order to avoid the risk that one bad container might survive and be consumed. The picture is further complicated since there is no way of determining just how long a particular container might be stored in a given household.

While alternatives to strict production and shelf life controls have undoubtedly been explored, there has been surprisingly little visible progress with repsect to other solutions to this problem. One such alternative solution, as suggested by the present invention, would be the provision of some sort of indicator which would readily and quickly show the condition of the food within the container. Certainly, the matter of displaying the ambient conditions within a particular sub-environment is not, in a broad sense, a new proposition. Fish aquarium thermometers and indoor-outdoor thermometers are common consumer products which provide a few examples. Various devices are also known which indicate the temperature, pressure, and/or humidity conditions within some sub-environment, and detectors are also known for indicating the presence of specific materials under these conditions.

Nevertheless, and put in its simplest terms, one cannot today walk into a supermarket and pick out a can of beans or mushrooms or whatever and tell at a glance whether or not there is a likely risk of botulism poisoning from this food. Obviously, a substantial need in this area has long existed, and continues to exist to this day. Further, from an economic standpoint, a reliable (even if not perfect) and inexpensive detector could well eliminate the need for shelf life controls, thus reducing or eliminating losses from the disposal of perfectly good food products. Additionally, it would substantially reduce the problem and risk resulting from further extending the storage once the product was taken home.

To explore the problem further, when the food within a sealed container starts to spoil, several by-products are given off. It is therefore theoretically possible to detect spoilage by detecting one or more of these by-products. Common to all such deterioration is the production of heat, acidity, pressure, and carbon dioxide ($CO_2$). Ideally, a spoilage detector should be useable with as many different food products as possible, without requiring different detectors for each different type of food material.

Turning to the first by-product, heat, it is easy to see that a heat detector is not likely to be practical because the heat evolved during spoilage is small. Thus the typical conditions of storage and transportation of many food containers would produce temperature conditions far in excess of those likely to result solely from the heat released during spoilage.

Similarly, acidity is not a preferred index since the pH of various foodstuffs varies widely. It would therefore be necessary to have a full spectrum of indicators in order to accommodate all the different pH levels.

Pressure is perhaps a slightly more workable indicator, but still not very practical. In the first place, due to temperature variations and the chance of mishandling before sale, such a detector would have to be unresponsive to nominal pressure changes. Also, many products are heat sterilized after the can is sealed, so such a pressure detector would have to be insensitive to the pressure increase developed when the can is sterilized. However, the development of substantial pressure occurs rather late in the spoilage process, and therefore, to be effective, it would be necessary for such a detector to respond to slight pressure increases. These are obviously conflicting requirements which make pressure detection impractical.

Thus, if it were possible simply to detect carbon dioxide gas, this would be an ideal way to indicate the likelihood that the food content of the container was deteriorating. Of course, such a detector should be usable with the widest possible variety of foodstuffs. Thus such a detector would have to operate independently of the other properties of foodstuffs, such as pH, salt content (corrosiveness), pressure or vacuum, and so on. Further, such a detector must obviously be approved for use in connection with consumables.

SUMMARY OF THE INVENTION

The present invention provides a detector for $CO_2$ gas in food containers which meets the above requirements. The invention uses a microporous plastic material to permit $CO_2$ gas to reach a $CO_2$ detector while preventing passage of liquids and solids. Thus, since liquids and solids cannot penetrate the microporous plastic, the $CO_2$ detecting medium is protected from contact with the food contents. As a result, the acidity or alkalinity of the basic foodstuffs does not affect the $CO_2$ detector. Further, since a thermally and pressure stable chemical detecting means is employed, the detector is usable with products regardless of the temperature and/or pressure conditions to which they may be subjected during manufacture, handling, and distribution. Only one thing is detected: excess $CO_2$ within the food container.

More particularly, the present invention provides a liquid impermeable pouch in which a liquid $CO_2$ detecting solution is entrapped. The solution provides a visually observable change when the concentration of $CO_2$ rises substantially above that which is the normal ambient concentration for our atmosphere. In the preferred embodiment, the indicator liquid is a solution of calcium hydroxide dissolved in water and having a molarity of approximately 0.19.

In one embodiment, one side of the pouch is formed of an inert plastic material which serves as a window through which the indicator may be observed Another portion of the pouch is formed of the gas permeable microporous plastic material, which may be, for example, a fluorinated ethylene propylene having a specific gravity less than approximately 2.18.

A suitable opening is formed in the container and the pouch is sealed into and over the opening so that the inert plastic material seals the opening and the microporous plastic portion is inside the container in at least gaseous contact or communication with the food contents. Thus, if $CO_2$ gas is generated it will pass through the microporous plastic and react with the calcium hydroxide to precipitate calcium carbonate. This causes the solution to change from clear to milky white, and this change is readily observable from outside the container by looking through the window. Visibility may be further enhanced by providing a coloring on the pouch opposite the window, such as green or blue. Such coloring provides a colored field which is visible until the $CO_2$ gas is produced. When the gas is produced, the observer sees the color of the window change from the color of the field to white, indicating that the food is probably spoiled and should not be consumed.

Many different pouch configurations are possible. The pouch may be formed of plastic sheets, or may be formed the colored window from solid plugs of plastic. A single sheet of plastic may be attached to a transparent wall or lid of a jar. The pouch may be formed integrally as part of a pull tab. Further, by using heat and cold resistant plastics it is possible to affix the spoilage indicator at any convenient time in the canning or bottling process. Thus, for example, can lids can be manufactured with the present invention incorporated therein well in advance of use, since the invention will not be adversely affected by the usual sterilization processes after the can is filled and sealed. Likewise, storage before use is no problem since the equalibrium constant of calcium hydroxide with a molarity of 0.19 requires approximately 5% $CO_2$ gas concentration to initiate precipitation of calcium carbonate. Since the atmospheric concentration of carbon dioxide is in the neighborhood of 0.3%, atmospheric $CO_2$ will not affect indicators which are left exposed to the air. Similarly, since the microporous plastic is liquid impermeable, the calcium carbonate solution will not dry out from storage under exposure to the atmosphere.

It is therefore an object of the present invention to provide a visual spoilage indicator for food containers which is usable on the widest possible variety of food containers, and usable in connection with the widest possible variety of foodstuffs; which provides a visual indication of the presence of $CO_2$ gas within the container; which provides such an indication independently of the particular pH of the food material; which is not adversely affected by the canning process itself; which has the longest possible shelf life both before and after incorporation into a food container; which includes a liquid impermeable pouch, a window forming a portion of the pouch, a gas permeable portion of the pouch, and an indicator means contained within the pouch for producing a change which is visually observable through the window when the concentration of $CO_2$ adjacent the gas permeable portion of the pouch substantially exceeds the ambient concentration of $CO_2$ in the atmosphere; and to accomplish the above objects and purposes in an inexpensive, compact configuration leading to the widest utilization possible.

BRIEF DESCRIPTION OF THE DRAWINGS

FIG. 1 is a perspective view of a metal food can incorporating one embodiment of the visual spoilage indicator in the lid thereof;

FIG. 2 is a fragmentary exploded view of the can lid, window, and microporous plastic portions of the indicator shown in FIG. 1;

FIG. 3 is a fragmentary cross sectional view of the indicator and can taken on line 3—3 of FIG. 1;

FIG. 4 is a top view of the FIG. 1 indicator illustrating the appearance of the indicator when no $CO_2$ has been detected, the dashed lines indicating a clear liquid;

FIG. 5 is a view similar to FIG. 4 illustrating the appearance following detection of $CO_2$, the liquid having now changed to a milky white appearance;

FIG. 6 illustrates another embodiment in which a detector according to the present invention is incorporated as part of an adhesively affixed plastic pull tab;

FIG. 7 is a fragmentary cross sectional view taken on line 7—7 of FIG. 6;

FIG. 8 is an exploded perspective illustrating another embodiment of the present invention incorporated into a translucent or transparent plastic lid;

FIG. 9 is a fragmentary cross sectional view taken on line 9—9 of FIG. 8; and

FIGS. 10 through 12 are fragmentary cross sectional views similar to FIG. 3 of three more embodiments of the invention.

DESCRIPTION OF THE PREFERRED EMBODIMENT

The present invention may be used with virtually any type of food container. For purposes of illustration, a typical tin can 10 having a lid 12 is shown in FIG. 1. A visual spoilage indicator 15 according to the present invention is attached to lid 12 across an opening 16 (FIGS. 2 and 3) provided in lid 12 for this purpose. The visual spoilage indicator 15 consists in part of a sheet of impermeable and inert clear plastic material 20 and a sheet of microporous plastic material 25. Sheet 25 has a cup 27 formed therein for receiving a $CO_2$ indicator such as an indicator solution 30. As illustrated in FIG. 3, sheets 25 and 20 are sealed to one another with cup 27 concavely facing sheet 20 to contain and seal the indicator solution between sheets 20 and 25 and in cup 27. The assembled indicator 15 is then sealed to the can lid 12 with cup 27 projecting through opening 16 into the interior 32 of the can 10. In the FIG. 3 embodiment sheets 20 and 25 are sealed to one another and to the can lid 12 by means of heat seals.

As may be seen, indicator 15 effectively forms a liquid impermeable pouch 35. The sheet of plastic 20 is transparent or translucent so that it forms a window 37 for the pouch 35. The microporous plastic sheet 25 forms a pouch portion which is gas permeable.

In a preferred embodiment the inert plastic sheet 20 was made of Lexan plastic, although any plastic of sufficient strength and approved for use on food containers would be appropriate. The microporous plastic sheet 25 was a fluorinated ethylene propylene, which may be referred to simply as a microporous "Teflon" membrane. The microporous "Teflon" membrane was selected to have a pore size large enough to pass carbon dioxide gas but too small to pass liquids, and thus had a specific gravity less than approximately 2.18. The indicator was simply a liquid solution of calcium hydroxide dissolved in water and having a molarity of approximately 0.19. With this molarity the calcium hydroxide is stable upon exposure to the atmosphere, but starts precipitating calcium carbonate when exposed to an atmospheric concentration of carbon dioxide of about 5% or more.

FIGS. 4 and 5 illustrate generally the appearance of the indicator 15 before and after the calcium hydroxide forms the calcium carbonate precipitate. Thus, if $CO_2$ has not been evolved in the container, the indicator 15 will have the clear appearance illustrated in FIG. 4. Once $CO_2$ appears, however, the indicator 15 will change to the white color illustrated in FIG. 5.

Of course, it is also possible to introduce certain variations to the preferred embodiment set forth above. For example, the indicator may be any appropriate material which provides a visual indication of the presence of carbon dioxide. Preferably, this material should also be approved for use with food materials. As an example, successful results have been obtained with a liquid solution of calcium hydroxide, citric acid, and meta-cresal purple indicator dissolved in water. The calcium hydroxide and citric acid are adjusted to provide the desired pH control, so that upon exposure to a concentration of $CO_2$ gas, the meta-cresal purple indicator changes from purple to yellow.

In another successful embodiment a microporous plastic material was used which consists of microporous acrylic polyvinyl chloride co-polymer on woven nylon cloth.

Another variation which was used successfully employed use of a microporous plastic sheet 25 which was colored blue. This is commercially available and is approved for use with food materials. The net effect is to provide a colored field for the pouch 35 which is opposite the window 37 formed by the plastic sheet 20, and behind the indicator solution 30. This provides a contrasting background for the indicator solution, so that the indicator as viewed in FIG. 4 appears blue and then changes to the white of FIG. 5 in the presence of the $CO_2$ gas. Other changes, such as from green to white, are of course also possible through the use of such a colored field behind the indicator solution.

More and more containers are now being provided with various types of pull tabs, and increasing numbers of these are made of plastic. FIGS. 6 and 7 illustrate an embodiment of the invention suitable for use with such a container. In this case, a plastic pull tab 40 is attached to a suitable can opening 42 by means of an adhesive 43. A piece of plastic or paper 44 is adhered to one end of the tab 40 to provide a pull 45 for engaging and removing the tab. In this embodiment, a microporous plastic sheet 46 having a cup 47 and enclosing an indicator solution 48 therein is attached to tab 40 by the same adhesive 43, and is located directly in the can opening 42. Tab 40 thus seals the indicator inside the can and also serves as a window for viewing the indicator solution 48.

FIGS. 8 and 9 illustrate still another embodiment which would be useful, for example, in home canning of foodstuffs. Here the lid 50 for a jar 52 consists of a sheet of transparent plastic which is held on the jar by a rim 53. A microporous plastic sheet 55 having a cup 56 is sealed to the underside of the lid 50 by an adhesive 57, and an indicator solution 58 is sealed within the cup 56.

FIG. 10 illustrates an indicator formed of a plug of material incorporated, for example, into a can lid such as illustrated in FIGS. 1–5. In this example, a plug 60 is formed of microporous plastic material and is sealed into an opening 61 by a cover sheet of impermeable, inert plastic material 62. Sheet 62 forms the window for the indicator, so that the indicator solution 63 is visible therethrough. As will be appreciated, even though a solid plug of material has been used, the plug 60 and cover sheet 62 form a pouch for containing the indicator solution. Plug 60 is hollowed out to provide a cup 64 which contains the indicator solution 63.

Similarly, FIG. 11 shows an embodiment in which a plug of substantially inert, impermeable plastic material is adhered in an opening 71 in the lid to provide a window for viewing the indicator solution 72 which is contained in a cup 73 hollowed out in plug 70. The bottom of the cup 73 is sealed by a sheet of microporous plastic material to seal the indicator solution 72 within the cup 73.

FIG. 12 illustrates still another embodiment which demonstrates that the particular order in which the permeable and impermeable portions of the pouch are joined to the container may be adjusted according to preferance and convenience. This embodiment is similar to those of FIGS. 3 and 7 except that the microporous plastic sheet 80 of this embodiment is attached to the inside of the can lid rather than the outside or the impermeable sheet. Sheet 80 contains the indictor solution 81 in a cup 82 formed therein, and these are sealed by a sheet of inert plastic material 84 attached across the outside of the can lid.

As may be seen, therefore, the present invention provides numerous advantages. It may be used with most of the food containers commonly in use today, and with most of the foods which are stored in these containers. It is not affected by temperature, pressure, or the pH of the food contents. It is stable, storable, and can endure the rigors of the canning process. It is inexpensive, easy to manufacture, and may be easily and readily incorporated into the food containers. In fact, it can be used anywhere within the container as long as it can be observed from the outside.

Perhaps of greatest importance, when a contamination product, such as $CO_2$, from deterioration of the food contents is present at the gas permeable portion of the pouch, the present invention provides a visual warning that the food contents may be deteriorated or contaminated. Thus unsafe containers which are evolving $CO_2$ gas may now be identified and discarded without waiting for the can to swell. Useful shelf life may be extended, and waste reduced.

While the method and article herein described constitute preferred embodiments of the invention, it is to be understood that the invention is not limited to this precise method and article, and that changes may be made therein without departing from the scope of the invention which is defined in the appended claims.

What is claimed is:

1. A visual spoilage indicator for food containers for providing a visual indication of the possibility of deterioration or contamination of the food contents by reasons of $CO_2$ evolution, comprising
    a. a liquid impermeable assembled plug of plastic material in an aperture in a lid of the food container,
    b. a window forming a portion of said plug,
    c. said plug also including a portion of microporous plastic which is $CO_2$ gas permeable and means forming a contrasting colored field opposite said window,
    d. means forming a cup in said plug for receiving an indicator means, and
    e. indicator means comprising an aqueous liquid calcium hydroxide solution at approximately 0.19 molarity sealed within said cup formed in said plug for producing a visible white calcium carbonate precipitate when the $CO_2$ level evolved upon deterioration of said food contents and passing through said gas permeable microporous plastic portion of said plug exceeds approximately a 5% $CO_2$ level, said visible white precipitate being observable through said window with the aid of said contrasting field opposite said window.

2. A food container including a visual spoilage indicator for providing a visual indication of the possibility of deterioration or contamination of the food contents, comprising:
    a. a wall structure forming said container,
    b. a liquid impermeable assembled plug of plastic material sealed in an aperture in said wall structure,
    c. a window forming a portion of said plug,
    d. said plug also including a portion of microporous plastic which is $CO_2$ gas permeable and means forming a contrasting colored field opposite said window,
    e. means forming a cup in said plug for receiving an indicator means, and
    f. indicator means comprising an aqueous liquid calcium hydroxide solution at approximately 0.19 molarity sealed within said cup formed in said plug for producing a visible white calcium carbonate precipitate when the $CO_2$ level evolved upon deterioration of said food contents and passing through said gas permeable microporous plastic portion of said plug exceeds approximately a 5% $CO_2$ level, said visible white precipitate being observable through said window with the aid of said contrasting field opposite said window.

* * * * *